US012605117B2

(12) United States Patent
Burg et al.

(10) Patent No.: US 12,605,117 B2
(45) Date of Patent: Apr. 21, 2026

(54) MAIN ELEMENT FOR AN ELECTROMEDICAL DEVICE, AND ELECTROMEDICAL DEVICE

(71) Applicant: OSYPKA AG, Rheinfelden-Baden (DE)

(72) Inventors: Benjamin Burg, Rheinfelden (DE); Thorsten Göttsche, Rheinfelden (DE)

(73) Assignee: OSYPKA AG, Rheinfelden-Baden (DE)

( * ) Notice: Subject to any disclaimer, the term of this patent is extended or adjusted under 35 U.S.C. 154(b) by 300 days.

(21) Appl. No.: 18/265,734

(22) PCT Filed: Feb. 21, 2022

(86) PCT No.: PCT/EP2022/054270
§ 371 (c)(1),
(2) Date: Jun. 7, 2023

(87) PCT Pub. No.: WO2022/179985
PCT Pub. Date: Sep. 1, 2022

(65) Prior Publication Data
US 2024/0041407 A1 Feb. 8, 2024

(30) Foreign Application Priority Data
Feb. 23, 2021 (DE) .......................... 102021104313.1

(51) Int. Cl.
*A61B 5/00* (2006.01)
*A61B 18/14* (2006.01)

(52) U.S. Cl.
CPC ........ *A61B 5/6852* (2013.01); *A61B 18/1492* (2013.01)

(58) Field of Classification Search
CPC .......................... A61B 5/6852; A61B 18/1492
See application file for complete search history.

(56) References Cited

U.S. PATENT DOCUMENTS

| | | | |
|---|---|---|---|
| 8,742,814 B2 | 6/2014 | Binder | |
| 2009/0240314 A1 | 9/2009 | Kong et al. | |
| 2019/0125440 A1 | 5/2019 | Oliverius et al. | |

FOREIGN PATENT DOCUMENTS

| | | |
|---|---|---|
| DE | 4329898 | 4/1995 |
| DE | 102017111280 | 11/2018 |

OTHER PUBLICATIONS

High-Sensitivity Pulse Oximeter and Heart-Rate Sensor for Wearable Health, Maxim Integrated, MAX30101, 32 pages, Jun. 2020.

*Primary Examiner* — Linda C Dvorak
*Assistant Examiner* — Abigail Bock
(74) *Attorney, Agent, or Firm* — Volpe Koenig

(57) ABSTRACT

Technical improvements in the field of electromedical devices, in particular of electromedical electrodes and/or electromedical catheters are provided. As an improvement, inter alia, a base element (1) for an electromedical device (2) is proposed, which includes, on a carrier element (3), at least one sensor module (4), at least one processing module (5), and at least one data line (6), to which the at least one processing module (5) of the base element (1) is connected. An electromedical device (2) can then be configured as needed from at least one base element (1) or preferably from multiple base elements (1).

12 Claims, 4 Drawing Sheets

31

4,5,
11,12,13,15,16,26,27,
28,29,30

6,22

3

2

4,5

9,11,12,13,14,15,
16,17,26,27,28

6,22

6,22

25

1

32

7,8

7,8

23    24

10

MAIN ELEMENT FOR AN ELECTROMEDICAL DEVICE, AND ELECTROMEDICAL DEVICE

CROSS-REFERENCE TO RELATED APPLICATIONS

This application is a 371 National Phase of International Application No. PCT/EP2022/054270, filed Feb. 21, 2022, which claims priority to German Patent Application No. 10 2021 104 313.1, filed Feb. 23, 2021, both of which are incorporated herein by reference as if fully set forth.

TECHNICAL FIELD

The invention relates to a base element for an electromedical device and an electromedical device, in particular an electromedical electrode or an electromedical catheter.

BACKGROUND

Electromedical devices, such as electromedical electrodes or also electromedical catheters, are used to carry out electromedical examinations and/or applications in the interior of the body of a patient. Depending on the embodiment of the electromedical device, for this purpose electromedical signals are recorded from the body and transmitted to a receiving unit having an evaluation unit of the electromedical device or also pulses from a medical pulse generator, for example a pacemaker, are delivered to a target tissue in the body of the patient.

SUMMARY

The object of the invention is to improve the usage properties of electromedical devices, such as electromedical electrodes or also electromedical catheters.

To achieve the object, first a base element for an electromedical device, in particular for an electromedical electrode and/or an electromedical catheter, is proposed, which includes the means and features of the independent claim directed to such a base element. To achieve the object, it is therefore proposed in such a base element that the base element includes a carrier element, on which at least one sensor module and/or at least one electromedical stimulation means, at least one processing module connected to the sensor module and/or to the stimulation means, and at least one data line are arranged, to which the processing module is connected.

At least one electromedical stimulation means, in particular a stimulation pole and/or an ablation pole, at least one photomedical stimulation means, in particular a stimulation diode, and/or at least one biochemical stimulation means can be provided, for example, as the at least one stimulation means.

The data line can be connected to a digital-electric transmission interface of the base element or a device equipped with the base element.

The sensor module can be designed so that the base element can be used as a base element of a sensing or mapping electrode.

Using the base element according to the invention and the functional units arranged thereon, namely the at least one sensor module, the at least one processing module, and the data line, a modular structure of an electromedical device is possible. Depending on the application, several of the above-mentioned base elements can be connected to one another and a tailor-made electromedical device can thus be provided.

A further special feature of the base element according to the invention consists in the processing module. Using the processing module, it is possible to convert sensor signals generated by the sensor module into processed data signals while still on board the base element and transmit them via the data line from the base element to a receiving unit connected at least indirectly to the base element, for example to an evaluation unit. By way of the processing module, the base element is equipped with computing power which enables processing of the sensor signals. This can contribute to the relief of a connected receiving unit.

The data line can comprise an electrical conductor and/or an optical conductor. If an optical conductor is used, an energy supply of the sensor module, the processing module, and/or the at least one stimulation means can possibly also be carried out optically by light.

In the processing of the sensor signals generated by the at least one sensor module, the processing module can already perform an evaluation and/or interpretation of the sensor signals and a conversion of the sensor signals into an evaluation variable to be monitored. In this way, it is possible with the aid of the processing module to infer an evaluation variable of interest from a physical variable monitored using the sensor module. In a specific exemplary embodiment, which is explained in more detail hereinafter, the sensor module can include, for example, a strain gauge and/or a force sensor and/or an acceleration sensor.

A deformation and/or spatial orientation of the base element may be inferred from the load, which can be ascertained using a strain gauge, for example, in consideration of further parameters, for example a rigidity and/or geometry of the carrier element of the base element. Precisely this interpretation of the physical variable acquired using the sensor module can be performed here with the aid of the processing unit on board the base element.

The processing module can thus be configured to process a sensor signal generated using the sensor module on the base element.

In one embodiment of the base element, which favors a modular structure of an electromedical device, such as an electromedical electrode or an electromedical catheter, it is provided that at least one attachment interface for attaching the base element to a different and/or structurally-identical base element, as is claimed by one of the claims directed to a base element, is formed on the carrier element of the base element. In this way, it is possible to connect the data lines of the base elements to one another via the connection interfaces of the base elements. Base elements connected to one another can thus be connected via a common data line to a receiving unit, for example an evaluation unit. Separate wiring for connecting the base elements can be superfluous in this case. Multiple base elements connected to one another can communicate with one another and with a connected receiving unit by means of a bus system.

To produce an electromedical device from multiple base elements, it can furthermore be expedient if at least one connection interface for connecting the base element to a different and/or structurally-identical base element according to one of the claims directed thereto is formed on the carrier element of the base element. The connection interface can be used in particular for mechanically connecting two base elements.

In one embodiment of the base element, it is provided that an attachment interface and/or a connection interface is formed by a solder pad on the base element. In this way, it is possible to connect two base elements, which are to be connected to one another, of an electromedical device both mechanically and for signaling via the connection interfaces and/or attachment interfaces formed as a solder pad. The above-mentioned digital-electrical transmission interface can be used as the attachment interface, for example.

In one embodiment of the base element, a processing module comprises an application-specific integrated circuit. The application-specific integrated circuit can be an ASIC. The application-specific integrated circuit can be configured, for example, to convert a sensor signal generated by the sensor module into an evaluation variable and/or to transmit the evaluation variable and/or the sensor signal via the data line of the base element to a receiving unit connectable at least indirectly to the base element, in particular an evaluation unit. In one embodiment of the base element, it is provided that the application-specific integrated circuit is configured to convert a sensor signal generated by a strain gauge and/or force sensor of the sensor module into a force as an evaluation variable and to transmit this evaluation variable via the data line to the above-mentioned receiving unit.

The base element, in particular the at least one sensor module of the base element, can include at least one strain gauge and/or at least one force sensor and/or at least one acceleration sensor and/or at least one biochemical sensor and/or at least one biosensor for biochemical physical states, in particular for detecting an inflammation, and/or at least one temperature sensor and/or at least one stimulation means. Such a stimulation means can be configured to deliver stimulation pulses to a target tissue of a patient, for example to nerve tissue and/or muscle tissue. At least one optical stimulation diode and/or at least one electromedical stimulation pole and/or an ablation pole explained in more detail hereinafter can be used, for example, as the at least one stimulation means.

In this way, it is possible to assign different functions to the base element according to the different sensor types and/or according to the stimulation means with which it can be provided. In an electromedical device explained in more detail hereinafter, which comprises different base elements of the above-explained type, it is possible that the base elements include different sensors and/or at least individual ones of the base elements also include at least one stimulation means, such as an optical stimulation diode and/or an electromedical stimulation pole. In this way, an electromedical device is created which comprises several of the above-mentioned base elements, to each of which different functions are assigned.

In order to produce a sensing and/or mapping electrode using the base element, the base element, in particular the at least one sensor module, can include at least one electromedical derivation pole. To also be able to perform ablation treatments, it is expedient if the base element, in particular the at least one sensor module, includes at least one electromedical ablation pole as a stimulation means. In this way, the base element and a device produced therefrom can be used to therapeutically influence a tissue. If the base element includes at least one electromedical stimulation means, the base element is suitable for producing an electromedical stimulation electrode.

It can be particularly advantageous if the base element includes a compensation means, for example a compensation circuit, which is configured for temperature compensation upon the processing of a sensor signal by the processing module. In particular in those sensor modules, the sensor signal generation of which is dependent on the ambient temperature, it can be advantageous to perform a compensation, thus a correction, for example, of the sensor signals generated in consideration of the ambient temperature, to which the base element is subjected during its use. This is with the goal of ensuring the most accurate possible monitoring of the physical variable using the sensor module and/or promoting accurate processing of the physical variable into an evaluation variable using the processing module. In this context, it can be particularly advantageous if the base module includes at least one temperature sensor, the measured values of which can be taken into consideration in the above-described compensation.

The base element, in particular the at least one sensor module, can furthermore include a detection device, in particular a detection circuit, for detecting, for example, a tissue state or tissue contact. For this purpose, the detection device can be configured, for example, for impedance measurement. This measurement is helpful to be able to better interpret signals derived from the examined tissue and/or to trigger a delivery of stimulation pulses to the tissue, preferably automatically, and/or possibly also to suppress it, for example because there is not sufficient contact with the tissue.

The carrier element of the base element can consist in one preferred embodiment of the base element of circuit board film, in particular of a blank made of circuit board film. In this way, it is possible to integrate the data line and, for example, also the above-mentioned at least one attachment interface or possibly also further attachment interfaces, for example for the at least one processing module and/or the at least one sensor module, into the circuit board film of the carrier element or to print them on the circuit board film and/or to deposit them thereon.

In one preferred embodiment of the base element, it is provided that the carrier element consists of a flat blank made of circuit board film, which is unfolded in the usage position of the base element to form a three-dimensional, preferably elongated body. In this way, the carrier element of the base element consisting of circuit board film obtains a high level of stability in consideration of the material use and intrinsic weight. In the usage position of the base element, the carrier element can be folded, for example, to form a three-dimensional body in the form of a preferably right prism or a cylinder.

The at least one sensor module of the base element can be arranged in the above-described base element on a side of and/or in a center of the carrier element, which forms an inside of the three-dimensional body. In this way, the sensor module of the base element is arranged well protected in the interior of the three-dimensional body of the base element. In one embodiment of the base element, the at least one processing module and/or the at least one data line can also be arranged on a side of the carrier element which forms an inside of the three-dimensional body. It is possible in this case that the sensor module and/or the at least one processing module and/or the at least one data line are arranged on the same inside of the three-dimensional body or also on different insides of the three-dimensional body.

In one embodiment of the base element, the data line can be integrated into the carrier element, in particular if the carrier element consists of circuit board film.

In one embodiment of the base element, in which the carrier element consists of a circuit board film, for example of a PCB film, the at least one data line and/or at least components of the at least one processing module and/or the at least one sensor module can be printed and/or deposited on the circuit board film.

An electromedical device having the features of the independent claim directed to such an electromedical device is also proposed to achieve the object. Therefore, in particular an electromedical device is proposed to achieve the object, which includes at least one base element according to one of the claims directed thereto. The electromedical device can be designed, for example, as an electromedical electrode and/or electromedical catheter.

In one embodiment of the electromedical device, it only includes a single base element. The base element can extend in this case from a distal to a proximal end of the device. If the device is designed as a catheter, the base element can also include an attachment cable, an attachment line, and/or a light guide, which can be connected to an evaluation unit and/or control unit of the device.

In one embodiment of the electromedical device, it is provided that it includes at least two base elements each according to one of the claims directed thereto. The processing modules of the base elements can be connected here to a common data line of the electromedical device. The common data line of the electromedical device can be assembled at least in sections in this case of the data lines of the base elements connected to one another of the electromedical device or can consist at least in sections of these data lines.

To provide the electromedical device with good stability, it can be expedient for two base elements connected to one another to at least partially mutually overlap.

Processing modules of base elements of the electromedical device can be part of a data bus system of the electromedical device. It is possible in this case that the processing modules of the base elements are connected to a common data line extending over the base elements of the electromedical device. The number of data lines can be minimized in this way.

In one embodiment of the electromedical device, it is provided that it includes a control unit and/or a receiving unit, in particular having an evaluation unit, to which its at least one base element is at least indirectly connected. The sensor signals of the sensor module processed using the processing module of the at least one base element can then be transmitted to the receiving unit of the electromedical device for further processing and/or evaluation.

Furthermore, it is possible that the electromedical device includes at least one medical pulse generator. The pulse generator can be, for example, an electromedical and/or photomedical pulse generator. In this way, electromedical and/or photomedical and/or biochemical pulses can be transmitted to at least one corresponding stimulation means of the electromedical device, which can be arranged or formed on a base element of the electromedical device, and can be delivered from there to a target tissue of a patient. An electromedical device in the form of a stimulation electrode, pacemaker electrode, and/or such a catheter can thus also be produced from the above-mentioned base elements.

The electromedical device can furthermore include an envelope, within which the at least one base element is arranged protected. An envelope tube can be provided as the envelope, for example. All base elements of the electromedical device are preferably arranged in a common envelope, in particular in a common envelope tube.

In one preferred embodiment, the electromedical device is designed as an electromedical electrode, in particular as a sensing electrode, mapping electrode, and/or ablation electrode. The device can be designed here in particular as an implantable electromedical electrode.

The electromedical device can also be designed as an electromedical catheter.

BRIEF DESCRIPTION OF THE DRAWINGS

The invention is described in detail hereinafter on the basis of an exemplary embodiment, but is not restricted to this exemplary embodiment. Further exemplary embodiments result by combining the features of individual or multiple claims with one another and/or in combination of individual or multiple features of the exemplary embodiment. In the figures:

DETAILED DESCRIPTION

Figure 5:
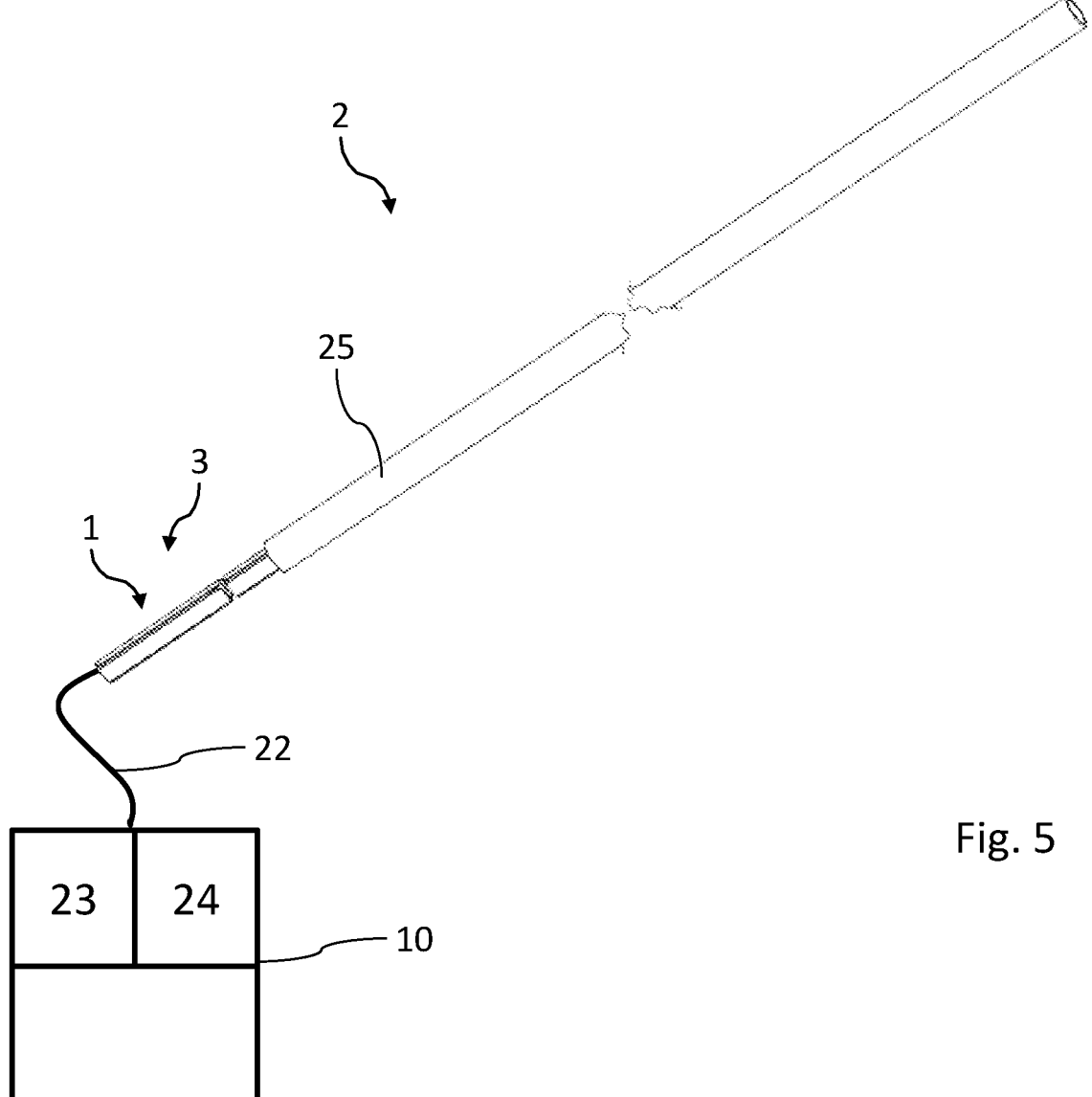
FIG. 5 shows an electromedical device in the form of an electromedical electrode having multiple base elements, as are shown in the preceding figures, wherein the base elements are arranged in an envelope tube of the electromedical device.

All figures show base elements, designated as a whole by 1, for an electromedical device 2. FIG. 5 shows an electromedical device 2 which comprises multiple base elements 1 connected to one another and which can be used as an electromedical electrode, in particular as an implantable electromedical electrode, or also as an electromedical catheter.

Figure 6:
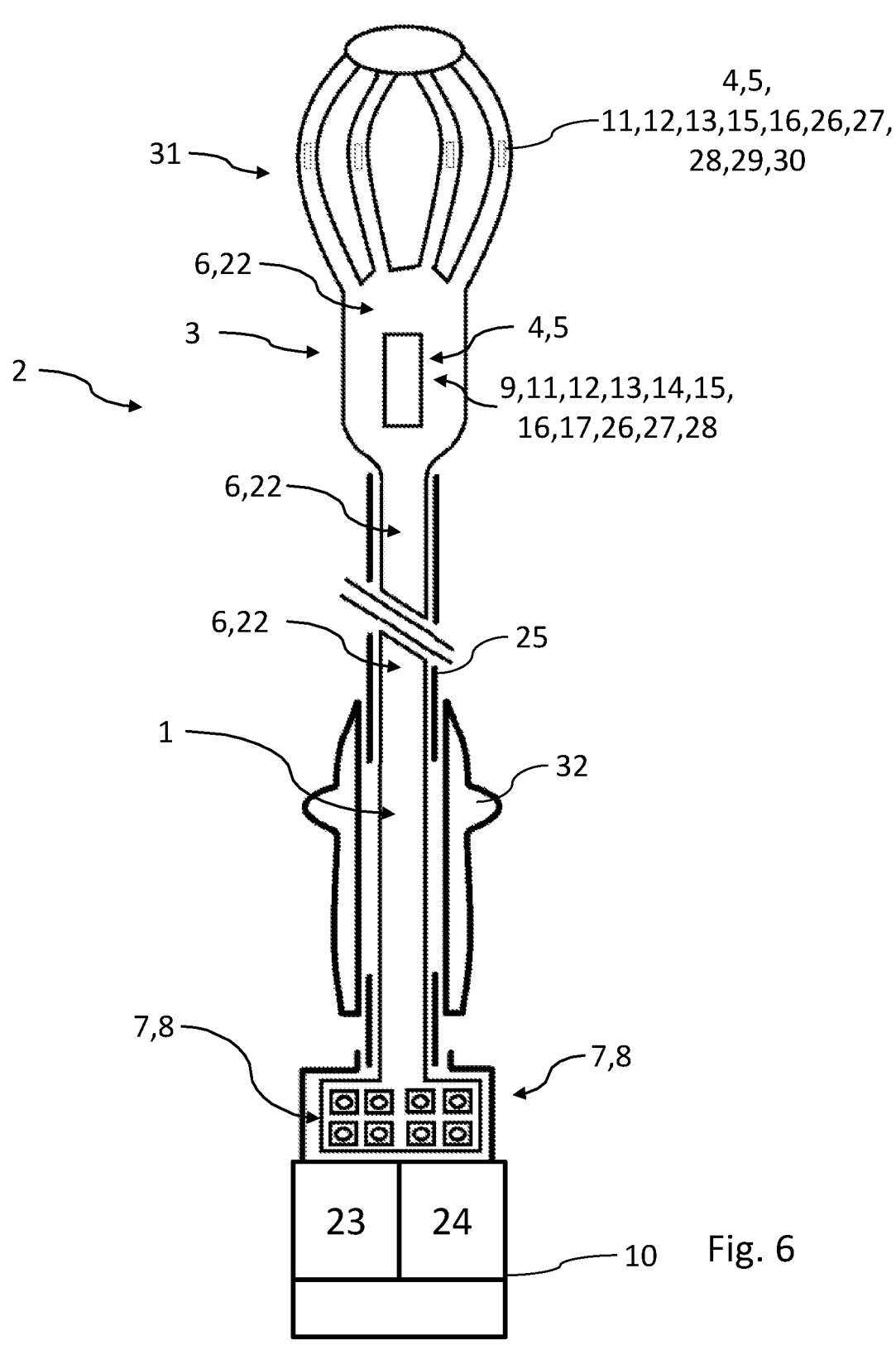
FIG. 6 shows a further embodiment of an electromedical device in a side view having a single base element and a basket at its distal end made up of catheter arms.

FIG. 6 shows a device 2 designed as a basket catheter, which only comprises a single base element 1 that extends from a distal end to a proximal end of the device 2.

In the following description of various embodiments of the invention, elements corresponding in their function receive corresponding reference numerals even in the event of differing design or formation.

Figure 1:
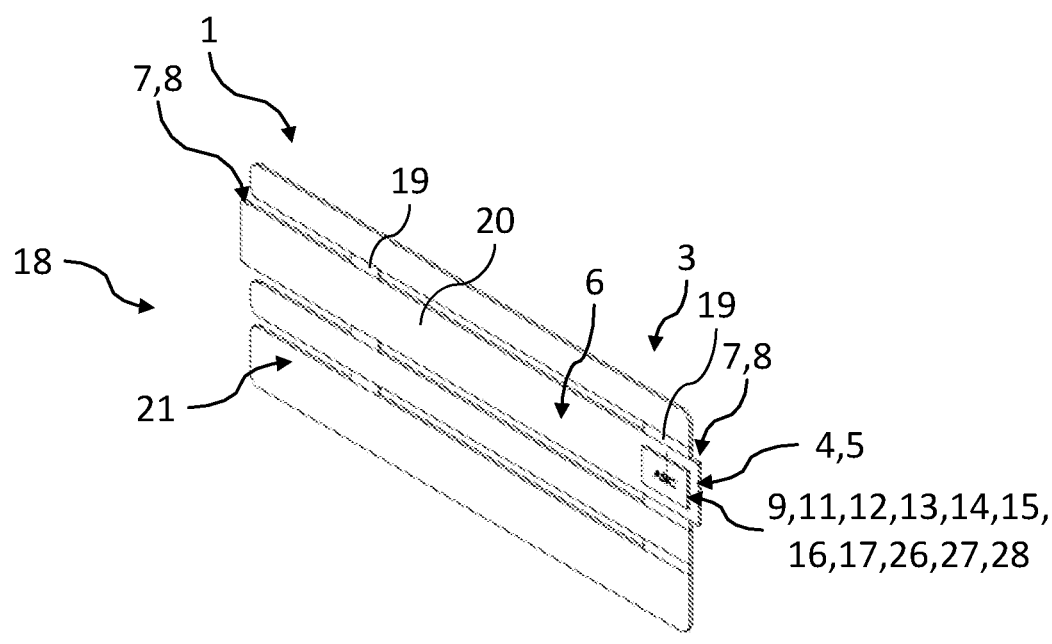
FIG. 1 shows an isometric illustration of a base element, which includes a carrier element made of circuit board film in the flat starting state, and is provided with a processing module and a sensor module on one side of the carrier element.

For example, FIG. 1 illustrates that the base element 1 includes a carrier element 3. A sensor module 4, a processing module 5 connected to the sensor module 4, and at least one data line 6, to which the processing module 5 is connected, are arranged on the carrier element 3. The data line 6 can be formed by an electrical and/or optical light guide.

The processing module 5 of the base element 1 is configured to process a sensor signal generated using the sensor module 4 while still on the base element 1. Two attachment interfaces 7 for attaching the base element 1 to different and/or structurally-identical base elements 1 are formed on the carrier element 3 of each base element 1. This is readily apparent on the basis of FIGS. 3, 4, and 5, each of which shows four base elements 1 connected to one another.

Furthermore, two connection interfaces 8 are formed on each of the carrier elements 3 of the base elements 1 for connecting, in particular for mechanically connecting, the respective base element 1 to different and/or structurally-identical base elements 1. In the base elements 1 shown in the figures, one attachment interface 7 and one connection interface 8 are combined in one interface in each case.

The attachment interface 7 and the connection interface 8 are formed by a solder pad on the carrier element 3 of the base element 1. Using a solder pad, it is possible to establish a signaling connection between the data lines 6 of the base elements 1, on the one hand, and a mechanical connection between the carrier elements 3 of the base elements 1, on the other hand.

The processing modules 5 of the devices 2 shown each comprise at least one application-specific integrated circuit 9. The circuits 9 of the base elements 1 are configured to convert a sensor signal generated by the respective sensor module 4 into an evaluation variable and to transmit the evaluation variable and/or if needed also the sensor signal of the sensor module 4 via the data line 6 to a receiving unit 10, which is at least indirectly connectable to the respective base element and is connected in the usage position.

Depending on the embodiment, the base elements 1, in particular the sensor modules 4 thereof, each include at least one strain gauge 11, at least one force sensor 12, at least one biochemical sensor 13, at least one biosensor 14 for biochemical physical states, in particular for detecting an inflammation, and/or at least one acceleration sensor 30 and/or at least one temperature sensor 26. Furthermore, the devices 2 are also equipped with derivation poles 27, via which electrical body signals can be recorded and sensing and/or mapping examinations can be carried out.

In particular the embodiment of the device 2 shown in FIG. 6 is particularly well suitable for carrying out sensing and/or mapping examinations due to the derivation poles 27 arranged at its catheter basket 31.

One of the base elements 1 of the devices 2 shown in the figures is moreover equipped with at least one stimulation means 15, 16, 28, for example an optical stimulation electrode 15 and also with at least one electromedical stimulation pole 16 and with at least one ablation pole 28. The above-mentioned sensors and also the above-mentioned stimulation diode 15 or the stimulation pole 16 can be arranged on the outside of the carrier element 3 of the respective base element 1 in the usage position. Pulses for ablating tissue can be delivered using the ablation pole 28.

Distal base elements 1 of the devices 1 shown are furthermore equipped with detection devices 29. The detection devices 29 are integrated into the sensor modules 4 and are configured for detecting a tissue state or tissue contact, for example by impedance measurement.

The base elements 1 are moreover equipped with a compensation means 17, for example a compensation circuit, which is configured for temperature compensation in the processing of a sensor signal by the processing module 5 of the respective base element 1 arranged on the carrier element 3.

In all base elements 1 which are shown in the figures, the carrier elements 3 consist of circuit board film.

Figure 2:
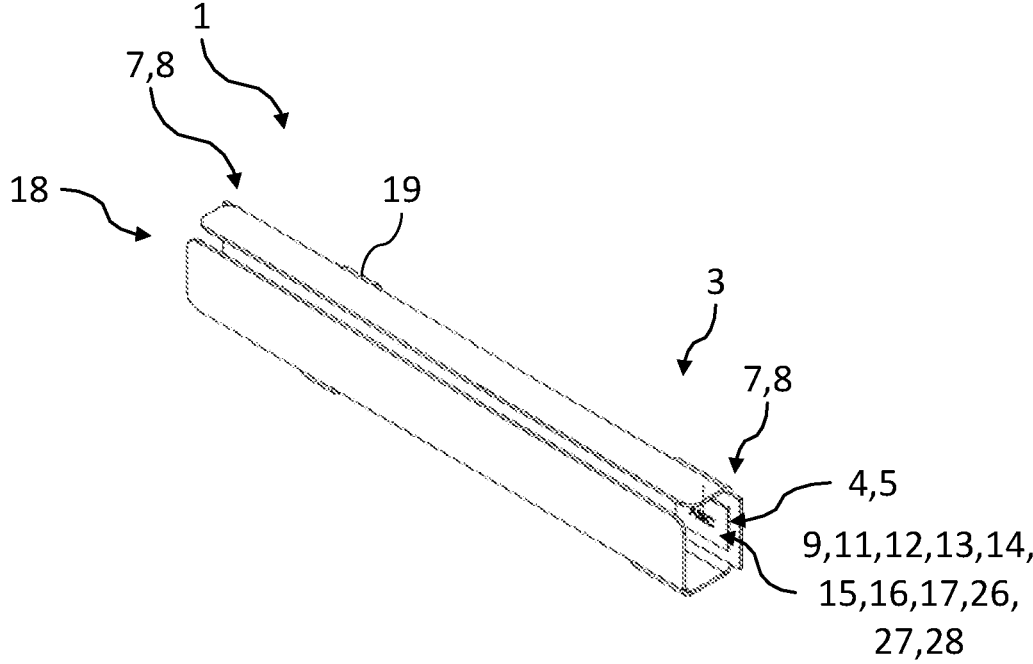
FIG. 2 shows the base element shown in FIG. 1 in the unfolded usage position.
Figures 3, 4:
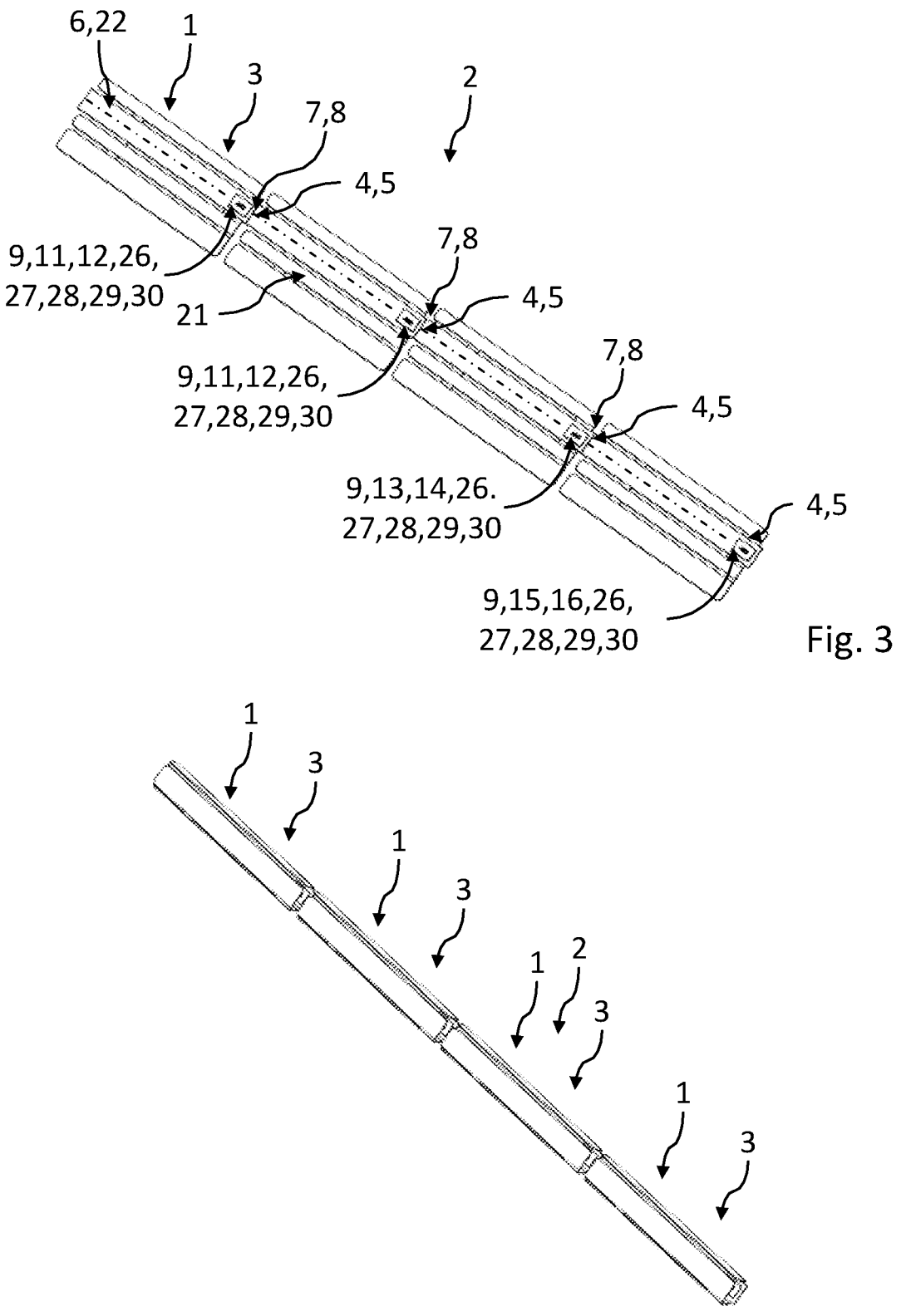
FIG. 3 shows a total of four base elements connected to one another via their attachment and connection interfaces, as are shown in FIGS. 1 and 2.
FIG. 4 shows the four base elements shown in FIG. 3 in the unfolded state in the unfolded position.

FIGS. 1 and 2 and also 3 and 4 illustrate that the carrier elements 3 of the base elements 1 each consist of a planar blank made of circuit board film. FIGS. 1 and 3 show the base elements 1 having their carrier elements 3 still as a flat blank. In the usage position, which is apparent in FIGS. 2 and 4 and also 5, the carrier elements 3 of the base elements 1 are each unfolded to form a three-dimensional elongated body in the form of a right prism. More precisely, the unfolded blanks of the carrier elements 3 include an imaginary envelope surface, which corresponds to that of a right prism.

The sensor module 4, the processing module 5, and also the data line 6 of each base element 1 are arranged on a side of the carrier element 3 which forms an inside 17 of the three-dimensional body, which the carrier element is unfolded to form in the usage position of the base element 1. As already mentioned above, sensors or also stimulation diodes 15 or stimulation poles 16 of the base elements 1 can be arranged on a side of the carrier element 3 which, in the folded state of the carrier element 3, forms an outside of the carrier element 3.

FIG. 1 clearly shows that the carrier element 3 comprises a total of four interconnected strips 18, 20 made of circuit board film. The strips 18, 20 are interconnected via connecting webs 19. The connecting webs 19 also function here as film hinges, which enable unfolding of the planar blank of the carrier element 3 from the position shown in FIG. 1 into the position shown in FIG. 2. It is noteworthy that the strip 20, on which the processing module 5 having the application-specific integrated circuit 9 is arranged, is longer than the other three strips 18 of the carrier element 3. It is clear from the illustration of the total of four interconnected carrier elements 3 according to FIG. 3 that a connection of the base elements 1 is performed to this longest strip 20 of the carrier elements 3. The attachment interfaces 7 and the connection interfaces 8 of the base elements 1 are also arranged on the longest strips 20.

It is to be mentioned in this case that an attachment interface 7 and a connection interface 8 are formed in each case at both free ends of each longest strip 20 of the respective carrier element 3. The data line 6 and also the attachment interfaces 7 and the connection interfaces 8 of the carrier elements 3 can be printed and/or deposited, for example, on the carrier elements 3. This is also true for attachment interfaces and/or components of circuits of the sensor modules 4, the processing modules 5, or also the compensation means 17.

FIG. 5 shows an electromedical device 2 in the form of an electromedical electrode or in the form of an electromedical catheter. The electromedical device 2 comprises multiple base elements 1, as are shown in FIGS. 1 to 4.

FIG. 6 shows an electromedical device 2 in the form of an electromedical electrode or in the form of an electromedical catheter. The electromedical device 2 comprises a single continuous base element 1, which extends from a distal to a proximal end of the device 2 and in the distal end area includes multiple arms, which are clamped to form a catheter basket 31. Some sensor modules 4 and in particular the derivation poles 27 and ablation poles 28 are arranged on the arms of the catheter basket 31. The catheter basket 31 forms an atraumatic tip of the device 2. Due to the catheter basket 31, the device 2 is well suitable for sensing and/or mapping, thus for creating stimulation maps of an examined tissue. The device 2 which is shown in FIG. 6 and is formed as a catheter includes a handle 32, using which it may be operated and positioned in the target tissue.

The processing modules 5 of the base elements 1 of the electromedical device 2 are connected to a common data line 22 of the electromedical device. The common data line 22 of the electromedical device 2 is formed at least in sections by the data lines 6 of the base elements 1.

FIGS. 3 and 4 indicate that two interconnected base elements 1 of the electromedical device 2 at least partially mutually overlap. The overlap takes place here at free ends of the longest strips 20 of the carrier elements 3 of the base elements 1.

The processing modules 5 of the base elements 1 of the electromedical devices 2 are part of a data bus system of the electromedical device 2. All processing modules 5 are connected to the common data line 22 of the electromedical device 2.

The electromedical device 2 is equipped with a receiving unit 10, which comprises an evaluation unit 23 and a medical pulse generator 24, and to which the base elements 1 of the electromedical device 2 are connected via the common data line 22.

The electromedical device 2 according to FIG. 5 furthermore includes an envelope 25, namely an envelope tube, within which the base elements 1 are arranged protected.

The invention relates to technical improvements in the field of electromedical devices, in particular electromedical electrodes and/or electromedical catheters. Among other things, a base element 1 for an electromedical device 2 is proposed as an improvement, which includes on a carrier element 3 at least one sensor module 4, at least one processing module 5, and at least one data line 6, to which the at least one processing module 5 of the base element 1 is connected. An electromedical device 2 can then be configured as needed from at least one base element 1 or preferably from multiple base elements 1.

LIST OF REFERENCE NUMERALS 1 base element
2 electromedical device
3 carrier element
4 sensor module
5 processing module
6 data line
7 attachment interface
8 connection interface
9 circuit
10 receiving unit
11 strain gauge
12 force sensor
13 biochemical sensor
14 biosensor
15 stimulation diode
16 stimulation pole
17 compensation means
18 strip
19 connecting webs
20 longest strip of 3
21 inside
22 common data line of 2
23 evaluation unit
24 pulse generator
25 envelope
26 temperature sensor
27 derivation pole
28 ablation pole
29 detection device
30 acceleration sensor
31 catheter basket
32 handle

The invention claimed is:

1. A base element (1) for an electromedical device (2), the base element comprising: a carrier element (3) comprising of circuit board film; at least one of a sensor module (4) or a stimulation means (15, 16, 28) arranged on the carrier element (3); a processing module (5) arranged on the carrier element (3) and connected to the at least one of the sensor module (4) or to the stimulation means (15, 16, 28); and a data line (6), to which the processing module (5) is connected.

2. The base element (1) as claimed in claim 1, further comprising at least one attachment interface (7) formed on the carrier element (3) that are-configured to attach the base element (1) to at least one of a different or structurally-identical one of the base elements (1).

3. The base element (1) as claimed in claim 2, wherein the attachment interface (7) is formed by a solder pad on the carrier element (3).

4. The base element (1) as claimed in claim 1, wherein the carrier element (3) consists of a planar blank made of circuit board film which is unfolded in a usage position of the base element (1) to form a three-dimensional body.

5. The base element (1) as claimed in claim 4, wherein at least one of the sensor module (4), the processing module (5), or the data line (6) are arranged on a side of the carrier element (3), which forms an inside (17) of the three-dimensional body.

6. The base element (1) as claimed in claim 1, wherein the sensor module (4) is provided and the processing module (5) is configured to process a sensor signal generated using the sensor module (4).

7. The base element (1) as claimed in claim 1, wherein the at least one processing module (5) comprises an application-specific integrated circuit (9) which is configured to at least one of a) convert a sensor signal generated by the sensor module (4) into an evaluation variable, b) to transmit the evaluation variable and/or the sensor signal via the data line (6) to a receiving unit (10) at least indirectly connectable to the base element (1).

8. The base element (1) as claimed in claim 1, further comprising at least one of a strain gauge (11), a force sensor (12), an acceleration sensor (30), a biochemical sensor (13), a biosensor (14) for biochemical physical states, a temperature sensor (26), an electrical derivation pole (27), a stimulation means, an optical stimulation diode (15), an electromedical stimulation pole (16), or an electromedical ablation pole (28).

9. The base element (1) as claimed in claim 1, further comprising a compensation means (17) which is configured for temperature compensation in processing of a sensor signal by the processing module (5).

10. The base element (1) as claimed in claim 1, further comprising a detection device (29) adapted for detecting a tissue state or tissue contact.

11. The base element (1) as claimed in claim 1, wherein at least one connection interface(s) (8) is formed on the carrier element (3) for connecting the base element (1) to at least one of a different or structurally-identical one of the base elements (1).

12. The base element (1) as claimed in claim 11, wherein the connection interface (8) is formed by a solder pad on the carrier element (3).

* * * * *